United States Patent [19]

Kambin

[11] Patent Number: 5,665,122
[45] Date of Patent: Sep. 9, 1997

[54] EXPANDABLE INTERVERTEBRAL CAGE AND SURGICAL METHOD

[76] Inventor: Parviz Kambin, 239 Chester Rd., Devon, Pa. 19333

[21] Appl. No.: 381,400

[22] Filed: Jan. 31, 1995

[51] Int. Cl.$^6$ ........................................ A61F 2/44
[52] U.S. Cl. ................... 623/17; 623/16; 411/55; 606/61; 606/63
[58] Field of Search .............. 623/16–17; 411/24–25, 411/55, 18, 21, 35; 606/61–63, 67

[56] References Cited

U.S. PATENT DOCUMENTS

| | | | |
|---|---|---|---|
| 925,006 | 6/1909 | Mason | 411/25 |
| 3,319,209 | 5/1967 | Reyenga | 411/21 |
| 4,011,602 | 3/1977 | Rybicki et al. | 623/16 |
| 4,401,112 | 8/1983 | Rezaian | 128/92 B |
| 4,553,273 | 11/1985 | Wu | 623/18 |
| 4,554,914 | 11/1985 | Kapp et al. | 128/92 C |
| 4,657,550 | 4/1987 | Daher | 623/17 |
| 4,743,256 | 5/1988 | Brantigan | 623/17 |
| 4,863,476 | 9/1989 | Shepperd | 623/17 |
| 4,878,915 | 11/1989 | Brantigan | 623/17 |
| 4,932,975 | 6/1990 | Main et al. | 623/17 |
| 5,015,247 | 5/1991 | Michelson | 606/61 |
| 5,026,373 | 6/1991 | Ray et al. | 606/61 |
| 5,059,193 | 10/1991 | Kuslich | 606/61 |
| 5,171,278 | 12/1992 | Pisharodi | 623/17 |
| 5,236,460 | 8/1993 | Barber | 623/17 |
| 5,344,252 | 9/1994 | Kamimoto | 41/55 |

FOREIGN PATENT DOCUMENTS 2015507  1/1991  Canada.

OTHER PUBLICATIONS

Biomat Brochure, Varlock Interbody Cage undated.

*Primary Examiner*—John G. Weiss
*Assistant Examiner*—Bruce E. Snow

[57] ABSTRACT

An expandable intervertebral cage apparatus includes a pair of cage components, each generally in the shape of a half cylinder. Each of the cage components provides a corresponding, abutting conically shaped recess that cooperates with a conical end portion of an expansion screw. One of the cage components carries a fitting with an internally threaded bore that receives external threads of the expansion screw. As the expansion screw advances into the cage, the conically shaped end portion of the expansion screw engages the conically shaped recesses on the cage components to expand the two cage components apart until they are in contact with the vertebral plates of adjacent vertebrae. The cage components have passageways for packing with bone-inducing-growth material allowing the cage to become part of a spinal fusion. A surgical method for installing the expandable intervertebral cage is also disclosed.

19 Claims, 3 Drawing Sheets

EXPANDABLE INTERVERTEBRAL CAGE AND SURGICAL METHOD

BACKGROUND OF THE INVENTION

1. Field of the Invention

The present invention relates to orthopedic prosthetic devices and particularly to an improved spinal cage prosthesis. Even more particularly the present invention relates to an expandable generally cylindrically shaped spinal cage prothesis that includes upper and lower components that can be incrementally separated from one another by an advancing screw until they are in contact with the vertebral plates of the involved spinal unit for use in vertebral fusion procedures. The present invention also relates to a surgical method for installing the spinal cage prothesis.

2. General Background

Surgical prosthetic implants have been developed for use in a surgical fusion of the vertebral column. These implants have been provided are in the form of a plug that is placed between two adjacent vertebrae. The plug contacts adjacent vertebral plates to achieve vertebral fusion, thus treating or preventing back pain in patients that have discogenic pain. Many spinal implants in the form of a cage or plug have been patented. An example of a patent for a surgical prosthetic implant that is used in vertebral interbody fusion is the Brantigan U.S. Pat. No. 4,743,256. The '256 patent discloses a surgical prosthetic implant for the vertebral column in the form of a rigid, preferably inert metal plug having a porous metal surface allowing ingrowth of bone cells for biologic fixation is provided to achieve vertebral interbody fusion for treating or preventing back pain. The plug forms a strut spanning and maintaining the disc space between adjoining vertebrae and has opposite ends bottomed in channels that are cut into the opposing faces of the vertebrae or opposed faces bottomed on the end faces of adjoining vertebrae. Bone ingrowth into the porous surface of the plug achieves long term biological fixation with living bone. Local bone graft harvested from the channel cuts into the vertebrae to receive the plug supplements the fusion. The implant minimizes or eliminates the need for bone graft material obtained from a second surgical site or from a bone bank and simplifies the method of achieving the interbody fusion.

In the Shepperd U.S. Pat. No. 4,863,476, there is disclosed a spinal implant that has an elongated body which is divided into two portions with mutually opposed contact surfaces and is for insertion into the joint space between two adjacent vertebrae. A cam device or cam devices are movable between the contact surfaces to expand or increase the spacing between the body portions so as to increase the spacing between the adjacent vertebrae.

The Brantigan U.S. Pat. No. 4,878,915 entitled "Surgical Prosthetic Implant Facilitating Vertebral Interbody Fusion" discloses a prosthesis plug forming transverse struts between adjacent vertebrae.

The Michelson U.S. Pat. No. 5,015,247 entitled "Threaded Spinal Implant" discloses an artificial implant which when placed between two adjacent vertebrae directly participates and is incorporated in the ensuing fusion.

The Ray U.S. Pat. No. 5,026,373 discloses a fusion cage having an external thread that can be surgically inserted into threaded bore extending laterally between the adjacent bony structures such as two vertebrae with the thread penetrating into cancellous bone of each of the vertebrae. The cage is easily screwed into place by hand without damage to bony structures. The cage is then packed with a bone-growth-inducing substances such as cancellous bone.

A middle expandable intervertebral disc implant is the subject of U.S. Pat. No. 5,171,278. The '278 patent discloses an artificial disc implant having a member for adapting in size and shape to an anatomical space between vertebrae and apparatus for expanding the member to conform to the space.

A Canadian Patent Application 2,015,507 discloses a spinal implant for use in surgical procedures for stabilizing the spine.

SUMMARY OF THE INVENTION

The present invention is an improvement to cage type expandable spinal prostheses. The apparatus includes an expandable spinal cage that is in an elongated cylindrical form for use in vertebral fusion procedures.

The expandable cage includes upper and lower component and includes an expansion screw. The expandable cage includes an exterior cylindrical extension that contains an external thread for attachment of a T-wrench inserter.

The interior of the extension is threaded to accommodate the expansion screw. The lower component includes an upwardly extending posterior protrusion which fits into and slides in a corresponding recess of the upper component.

When the expansion screw is turned clockwise using a wrench, the upper and lower components are separated from one another until they are in contact with the vertebral plates of adjacent vertebrae.

The cage components can have passageways for packing with bone-inducing-growth material allowing the cage to become part of the fusion. The cage components can have bone graft or other osteoinductive or osteoconductive substance thereon for the purpose of enhancing bone fusion.

Also disclosed is a method for surgically installing the expandable spiral prothesis comprising the steps of preparing a space between two vertebrae for receiving the prothesis, surgically inserting the prothesis into the resulting space and advancing a screw member to separate incrementally the upper and lower cage components.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
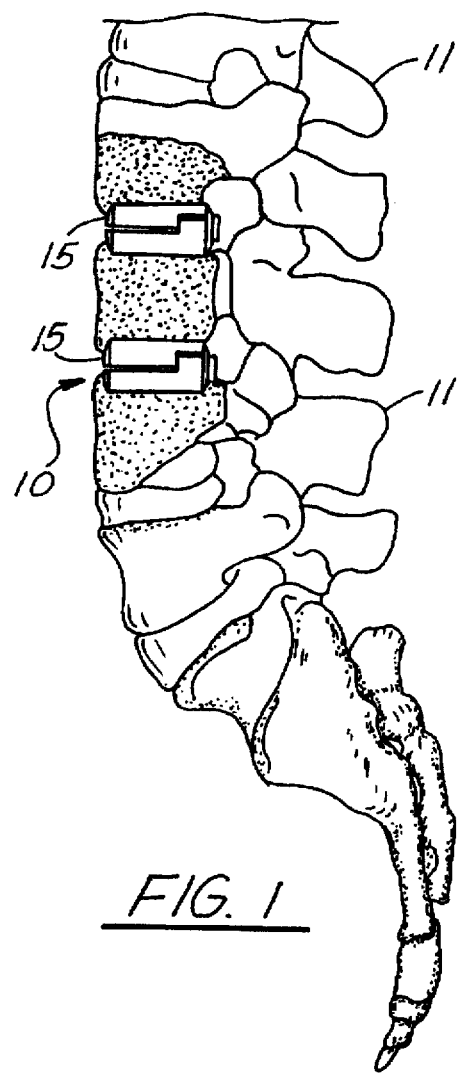
FIG. 1 is a sectional elevational view of a patient's spine showing placement of the preferred embodiment of the apparatus of the present invention.

FIGS. 1-10 show the preferred embodiment of the apparatus of the present invention designated generally by the numeral 10. In FIG. 1, spinal cage prosthesis 10 is shown applied to a patient's spine 11 between adjacent vertebrae 12, 13. Two of the spinal cages 10 are shown placed in the intervertebral space 14 between vertebrae 12, 13. The cage can be implanted via a variety of surgical techniques. These techniques include both open procedures from the anterior or posterior aspect of the body. In concept, these surgical approaches would be similar to existing anterior or posterior lumbar interbody fusion procedures (ALIF, PLIF) with the exception of the boney preparation. In addition, the device could be implanted in a closed surgical technique through a transcutaneous cannula system. This cannula could enter the body cavity from a variety of directions, including posterior-lateral, or anterior.

After implantation, the cage prosthesis 10 is expanded so that it contacts the vertebral plates of adjacent vertebrae 12, 13 as part of a vertebral fusion procedure.

Figure 2:
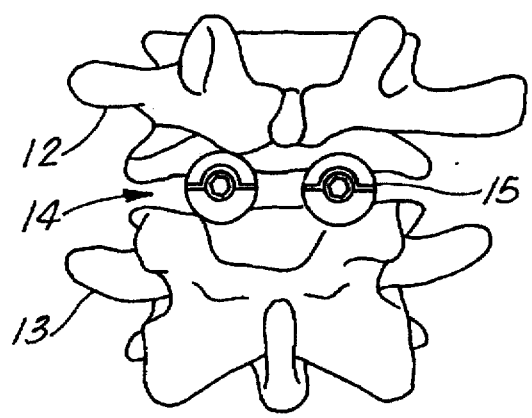
FIG. 2 is an elevational frontal view of the preferred embodiment of the apparatus of the present invention.
Figure 3:
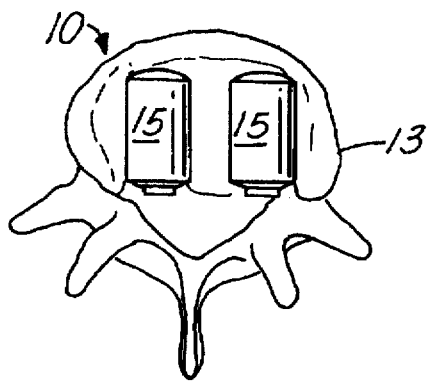
FIG. 3 is a top view of the preferred embodiment of the apparatus of the present invention.
Figure 4:
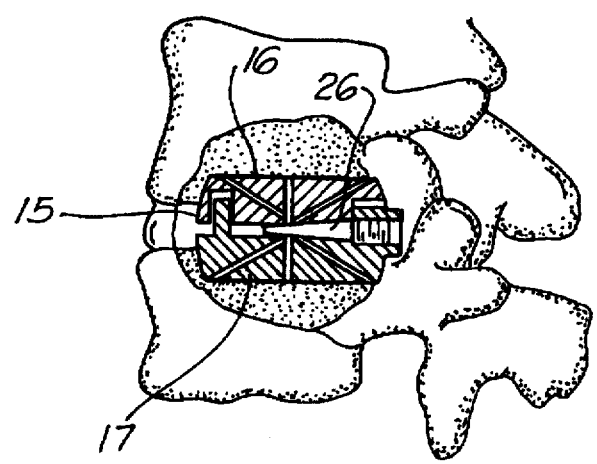
FIG. 4 is a sectional view of the preferred embodiment of the apparatus of the present invention.

Spinal cage apparatus 10 is shown in FIGS. 2 and 3 as placed during a spinal fusion procedure. In FIGS. 4-10, spinal cage prosthesis 10 is shown more particularly. The apparatus 10 includes a two part cage body 15 having upper and lower cage sections 16, 17. The overall cage 15 presents a cylindrical shape. The upper cage section 16 provides a half cylinder shaped outer surface 18. The cage section 17 provides a similarly shaped, curved half cylinder outer surface 19. The surfaces 18, 19 are preferably roughened. Examples of roughened surfaces include for example a threaded or hurled surface, or a surface covered with short spikes that would engage the end plates of the vertebral bodies. The purpose of the roughening of the surfaces 18, 19 is to enhance fixation of cage body 15.

Each of the cage sections 16, 17 provides abutting flat surfaces 20, 21, the surfaces 20, 21 aligning in face-to-face relation upon assembly as shown in FIGS. 4-9.

Figure 5:
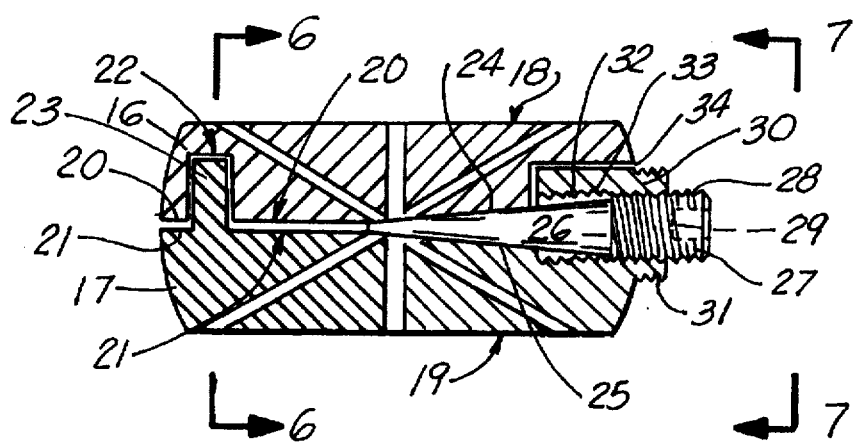
FIG. 5 is a sectional view of the preferred embodiment of the apparatus of the present invention.
Figure 6:
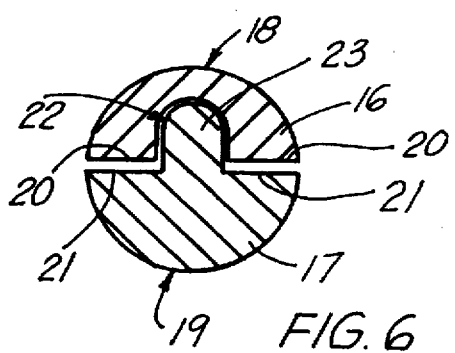
FIG. 6 is sectional view taken along lines 6—6 of FIG. 5.
Figure 7:
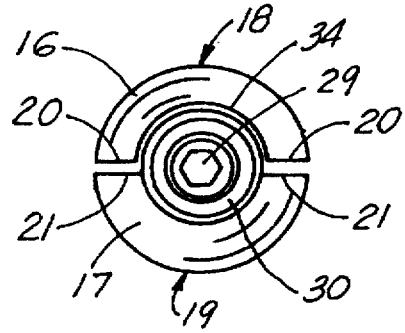
FIG. 7 is a sectional view taken along lines 7—7 of FIG. 5.
Figure 8:
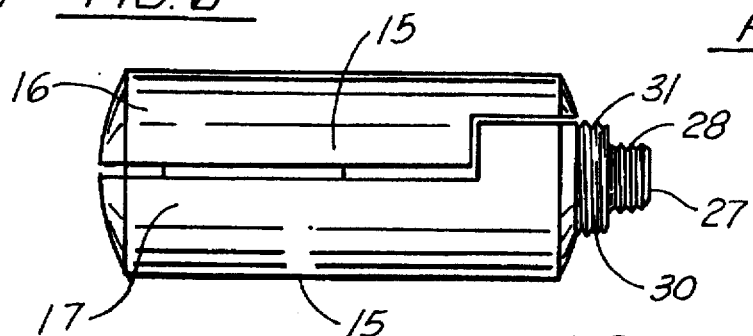
FIG. 8 is a side view of the preferred embodiment of the apparatus of the present invention.
Figure 9:
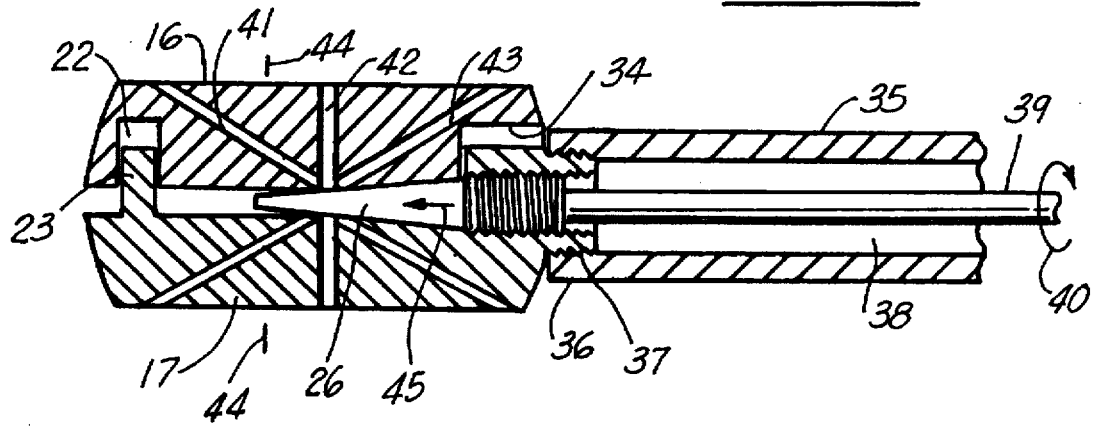
FIG. 9 is a side sectional view of the preferred embodiment of the apparatus of the present invention shown attached to a T-wrench inserter.
Figure 10:
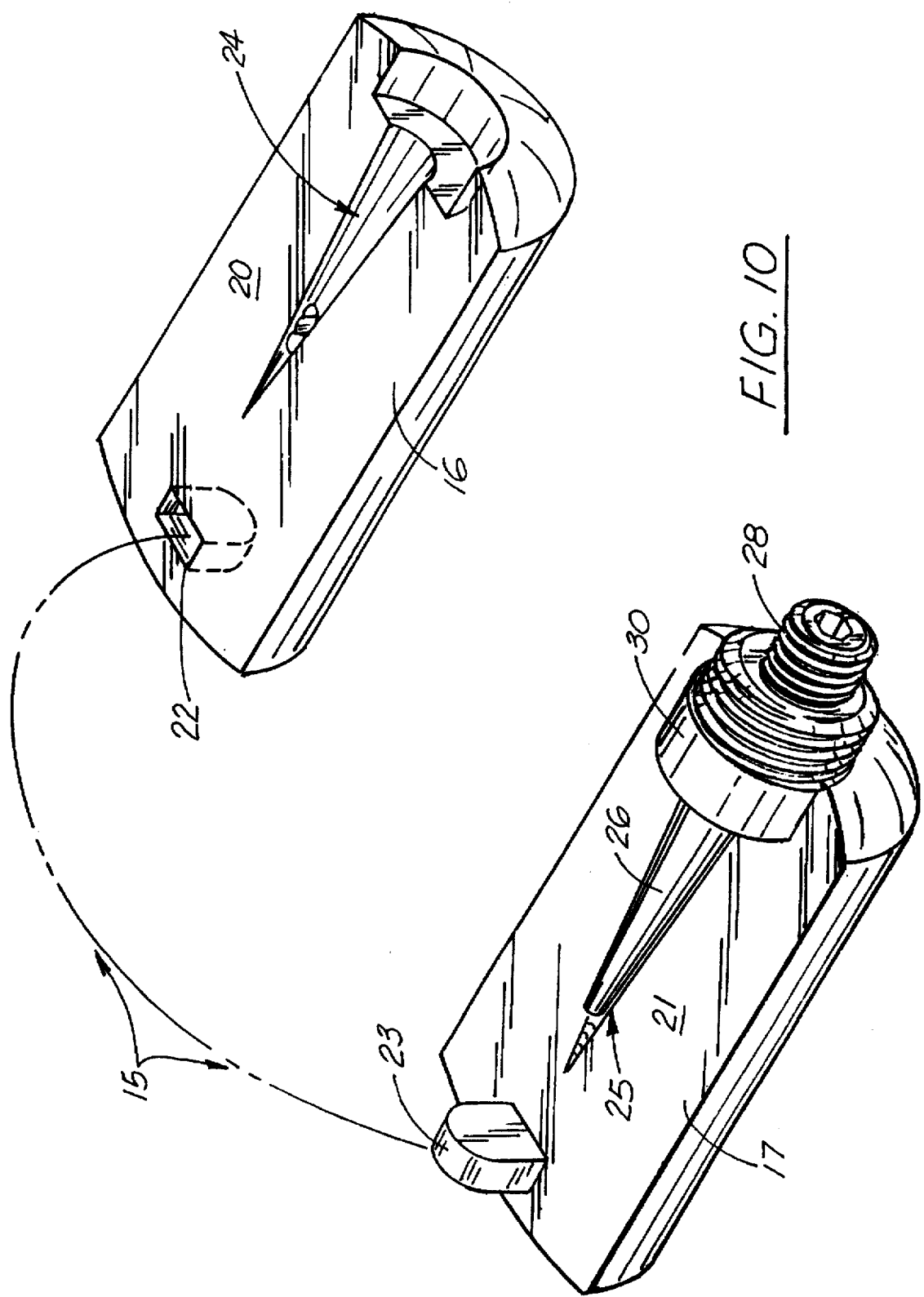
FIG. 10 is an exploded perspective view of the preferred embodiment of the apparatus of the present invention.

Socket 22 of cage section 16 cooperates with projection 23 of cage section 17 to form a sliding and telescoping connection. In FIG. 5, the cage sections 16, 17 are shown in a collapsed position. In FIG. 9, the cage sections 16, 17 are shown in an expanded position, wherein the projection 23 slides in a direction away from socket 22 as shown.

A pair of corresponding, conically shaped surfaces 24, 25 cooperate with the conically shaped end 26 of expansion screw 27. As the screw 27 advances, the conical end 26 engages conically shaped recess 24, 25 of cage sections 16, 17 respectively. The conical end 26 forces the two cage sections 16, 17 apart as the expansion screw 27 advances in the direction of arrow 45 in FIG. 9. In FIG. 9, arrows 44 illustrate the expansion of cage member 16, 17 apart as expansion screw 27 advances in the direction of arrow 45. Expansion screw 27 has a cylindrically shaped section covered with external threads 28 and a hexagonal socket 29 that receives a hexagonal wrench 39.

Anterior fitting 30 provides external threads 31 for receiving a T-wrench inserter 35 as shown in FIG. 9. Anterior fitting 30 includes a cylindrical bore 32 with internal threads 33 receptive of the external threads 28 of expansion screw 27 as shown in FIGS. 5 and 9. Upper cage section 16 has an arcuate recess 34 that accommodates anterior fitting 30. In the preferred embodiment, the fitting 30 can be a part of the lower cage section 17, being integral therewith.

T-wrench inserter 35 has a distal end 36 with an internally threaded section 37. The internally threaded section 37 engages external threads 31 of fitting 30 during use. Inserter 35 has a cylindrically shaped hollow bore 38 allowing hexagonal wrench 39 to extend therethrough so that it can engage the hexagonal socket 29 of expansion screw 27.

Curved arrow 40 in FIG. 9 illustrates the rotation of hexagonal wrench 39 during an insertion of expansion screw 27 in the direction of arrow 45.

Cage 15 can include a plurality of open ended bores or passageways 41-43. These passageways 41-43 allow for packing with bone-inducing-growth material that allows the cage 15 to become part of the fusion. Other bone graft or other osteoinductive or osteoconductive substances could be included with cage 15 for the purpose of enhancing bone fusion.

According to the method of the present invention for providing intervertebral interbody fusion in the vertebral column, the surgeon initially prepares the intervertebral space 14 shown in FIG. 2. The T-wrench inserter 35 may then be coupled to the anterior fitting 30 on the cage body 15. The cage body 15 is surgically inserted into the intervertebral space 14. A hexagonal wrench 39 is inserted into the hexagonal socket 29 in the end of the expansion screw 27. Upon rotation of the hexagonal wrench in a clockwise manner, the expansion screw 27 transverses laterally in the direction indicated by arrow 45 in FIG. 9 as described above to separate incrementally the upper and lower cage sections 16 and 17.

The following table lists the parts numbers and parts descriptions as used herein and in the drawings attached hereto.

Parts List

| Part Number | Description |
| --- | --- |
| 10 | spinal cage prosthesis |
| 11 | spine |
| 12 | vertebrae |
| 13 | vertebrae |
| 14 | intervertebral space |
| 15 | cage body |
| 16 | upper cage section |
| 17 | lower cage section |
| 18 | cylindrical outer surface |
| 19 | cylindrical outer surface |
| 20 | flat surface |
| 21 | flat surface |
| 22 | socket |
| 23 | projection |
| 24 | conically shaped surface |
| 25 | conically shaped surface |
| 26 | conical end |
| 27 | expansion screw |
| 28 | external threads |
| 29 | hexagonal socket |
| 30 | anterior fitting |
| 31 | external threads |
| 32 | cylindrical bore |
| 33 | internal threads |
| 34 | arcuate recess |
| 35 | T-wrench inserter |
| 36 | distal end |
| 37 | internal threaded section |
| 38 | cylindrical bore |
| 39 | hexagonal wrench |
| 40 | arrow |
| 41 | passageway |
| 42 | passageway |
| 43 | passageway |

-continued

| Part Number | Description |
|---|---|
| 44 | arrow |
| 45 | arrow |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A bio-compatible intervertebral prosthesis for implantation between adjacent vertebrae comprising:
    a) a cage body that includes a plurality of components including at least first and second separable cage sections configured and sized to be inserted between adjacent vertebrae;
    b) said cage sections being separable along the longitudinal axis of said cage body;
    c) the cage body having an anterior section with an internally threaded bore;
    d) the cage body having an internal recess defined by a recess surface;
    e) the cage body having anterior and posterior end portions;
    f) An expansion screw with proximal and distal end portions, the proximal end having means thereon for forming a connection with a rotary driver for rotating the screw, the distal end portion being sized and shaped to force the first and second cage sections apart as the screw advances longitudinally within the cage body to engage the recess surface along the length of the distal end of said expansion screw and in a direction from the anterior to the posterior end portions thereof;
    g) wherein said expansion screw has a length less than the length of the cage body and wherein said expansion screw does not extend beyond the end of said cage body; and
    h) wherein the first and second cage sections move apart incrementally as the screw advances into the internally threaded bore and recess surface.

2. The apparatus of claim 1, wherein the cage body has an outer surface with a generally cylindrical shape.

3. The apparatus of claim 1 wherein the cage body sections each have corresponding flat abutting surfaces.

4. The apparatus of claim 1 wherein the cage body recesses are generally conically shaped.

5. The apparatus of claim 1 wherein each of the cage sections has a recess portion that engages the expansion screw.

6. The apparatus of claim 1 wherein the distal end of the expansion screw is conically shaped.

7. The apparatus of claim 1 wherein the anterior section includes an anterior fitting that carries the internally threaded bore.

8. The apparatus of claim 1 wherein the expansion screw has a cylindrically shaped threaded section and a conically shaped unthreaded section.

9. The apparatus of claim 1 wherein the cage body sections are slideably attached at the posterior end portion thereof.

10. A bio-compatible intervertebral prosthesis for implantation between adjacent vertebrae comprising:
    a) a cylindrically shaped cage body that includes at least first and second separable sections configured and sized to be inserted between adjacent vertebrae, each section having a flat inner surface portion that engages the flat inner surface of the other component;
    b) said separable sections being separable along the longitudinal axis of said cage body;
    c) the cage body having an anterior fitting integral thereto with an internally threaded bore;
    d) the cage body having anterior and posterior end portions;
    e) each of the cage body sections having a conically shaped internal recess with a bearing surface;
    f) an externally threaded expansion screw that engages the internal threads of the fitting, the screw having proximal and distal end portions, the proximal end having a tool receptive socket thereon for forming a connection with a rotary driver tool that can rotate the screw, the distal end portion being sized and shaped to force the first and second components apart as the screw advances longitudinally within the cage body to engage the recess surface along the length of the distal end of said expansion screw and in a direction from the anterior to the posterior end portions thereof;
    g) wherein said expansion screw has a length less than the length of the cage body and wherein said expansion screw does not extend beyond the end of said cage body; and
    h) wherein the first and second sections move apart incrementally as the screw advances into the internally threaded bore and recess surface.

11. The apparatus of claim 10 further comprising means for receiving bone graft material.

12. The apparatus of claim 10 further comprising bore means for receiving bone fusion augmenting material.

13. The apparatus of claim 10 further comprising roughened surface means on the outer bone engaging surface of at least one of the components for enhancing fixation of the cage body to the patents vertebral bodies.

14. The apparatus of claim 10 wherein at least one of the components has a roughened surface for engaging the end plates of the patient's vertebral bodies.

15. The apparatus of claim 10 wherein the tool receptive portion is a socket.

16. A bio-compatible intervertebral prosthesis for implantation between adjacent vertebrae comprising:
    a) a cylindrically shaped cage body that includes at least first and second separable cage sections configured and sized to be inserted between adjacent vertebrae, each having
    b) a flat inner surface portion that engages the flat inner surface of the other component;
    c) said separable sections being separable along the longitudinal axis of said cage body;
    d) the cage body having an anterior fitting integral thereto with an internal bore;
    e) the cage body having anterior and posterior end portions;
    f) each of the cage body sections having a conically shaped internal recess surface with a bearing surface;
    g) An expansion pin that engages the bore of the anterior fitting, the pin having proximal and distal end portions, the proximal end having a tool receptive portion thereon for forming a connection with a driver tool that can manipulate the pin, the distal end portion being sized and shaped to force the first and second sections apart as the pin advances longitudinally within the cage body to engage the recess surface along the length of the distal end of said expansion screw in a direction from the anterior to the posterior end portions thereof;

h) wherein said expansion screw has a length less than the length of the cage body and wherein said expansion screw does not extend beyond the end of said cage body; and i) wherein the first and second sections move apart incrementally as the pin advances into the bore and recess surface.

17. The apparatus of claim 16 wherein the expansion pin is a threaded expansion screw.

18. The apparatus of claim 16 wherein the cage body bore is threaded.

19. A method for providing bio-compatible vertebral interbody fusion in the vertebral column comprising the steps of:

a) preparing a space for receiving an orthopedic prosthetic device between two vertebrae;

b) surgically inserting a substantially cylindrically shaped spinal cage body into the space between the vertebrae, wherein the spinal cage includes upper and lower cage sections; each of the cage body sections having an internal recess with a bearing surface; and c) advancing a unitary screw member to separate incrementally the upper and lower cage sections; wherein said screw member has a length less than the length of the cage body and does not extend beyond the end of said cage body and wherein the screw member includes a distal end portion being sized and shaped to engage the recess surface of the first and second cage sections and to force the first and second cage sections apart as the screw advances longitudinally into the cage body.

* * * * *

UNITED STATES PATENT AND TRADEMARK OFFICE
CERTIFICATE OF CORRECTION

PATENT NO. : 5,665,122
DATED : September 9, 1997
INVENTOR(S) : Parviz Kambin

It is certified that error appears in the above-indentified patent and that said Letters Patent is hereby corrected as shown below:

Front Page of Patent:

Attorney, Agent or Firm-- James W. Pravel

Signed and Sealed this

Twenty-fifth Day of November, 1997

Attest:

BRUCE LEHMAN

Attesting Officer        Commissioner of Patents and Trademarks